(12) United States Patent
Long et al.

(10) Patent No.: US 9,958,370 B2
(45) Date of Patent: May 1, 2018

(54) METHOD FOR MEASURING DIFFUSION PERFORMANCE OF ACID DYE IN COLOR PASTE

(71) Applicant: NANTONG TEXTILE & SILK INDUSTRIAL TECHNOLOGY RESEARCH INSTITUTE, Nantong, Jiangsu (CN)

(72) Inventors: Jiajie Long, Zhangjiagang (CN); Feng Chen, Zhangjiagang (CN)

(73) Assignee: NANTONG TEXTILE & SILK INDUSTRIAL TECHNOLOGY RESEARCH INSTITUTE, Nantong (CN)

( * ) Notice: Subject to any disclaimer, the term of this patent is extended or adjusted under 35 U.S.C. 154(b) by 98 days.

(21) Appl. No.: 15/125,648

(22) PCT Filed: Aug. 11, 2014

(86) PCT No.: PCT/CN2014/084094
§ 371 (c)(1),
(2) Date: Sep. 13, 2016

(87) PCT Pub. No.: WO2015/188435
PCT Pub. Date: Dec. 17, 2015

(65) Prior Publication Data
US 2017/0003211 A1 Jan. 5, 2017

(30) Foreign Application Priority Data

Jun. 10, 2014 (CN) .......................... 2014 1 0256338

(51) Int. Cl.
*G01N 13/00* (2006.01)
*G01N 21/31* (2006.01)
*G01N 21/33* (2006.01)

(52) U.S. Cl.
CPC .......... *G01N 13/00* (2013.01); *G01N 21/3103* (2013.01); *G01N 21/33* (2013.01); *G01N 2013/003* (2013.01)

(58) Field of Classification Search
CPC ..... G01N 13/00; G01N 21/33; G01N 21/3103
See application file for complete search history.

(56) References Cited

FOREIGN PATENT DOCUMENTS

CN 104034633 A 9/2014

OTHER PUBLICATIONS

Kato, Hiroshi, Diffusion of Acid Dyes in Silk, 1978, Sen'i Gakkaishi, vol. 34, No. 7, pp. 71-78.*

(Continued)

*Primary Examiner* — Lisa Caputo
*Assistant Examiner* — David Z Huang
(74) *Attorney, Agent, or Firm* — SZDC Law P.C.

(57) ABSTRACT

The invention provides a method for measuring the diffusion performance of an acid dye in a color paste, comprising preparing a primary paste and placing the primary paste into a transparent cylindrical container; adding a dye to the primary paste formulate a color paste, and flatly and uniformly paving a layer of the color paste on an upper surface of the primary paste; performing constant-temperature treatment at 60-95° C. on the cylindrical container, so that the dye in the color paste on the top of the blank primary paste in the cylindrical container diffuses downwards to the bottom of the cylinder; and sampling the primary paste from a sampling hole, and diluting the sampled primary paste with deionized water. The method of the invention has simple operation steps, reliable and safe experiments, highly stable test data and good reproducibility of results, and high temperature and high pressure are not required herein.

9 Claims, 2 Drawing Sheets

(56) References Cited

OTHER PUBLICATIONS

Brody, H., Overdyeing and Diffusion of Acid Dyes in Nylon, Sep. 1965, Textile Research Journal, pp. 844-850.*
Cheung, W.H., et al., Intraparticle diffusion processes during acid dye adsorption onto chitosan, Nov. 15, 2006, Bioresource Technology 98, pp. 2897-2904.*
"Determination of dye diffusion properties" GB/T27597-2011, Dec. 2, 2011 (Dec. 5, 2011), pp. 433-435.
Jia, Tenghong. "Diffusion on silk of acid dyes" "Textile Technology Overseas (chemical fiber, dyeing and finishing, three wastes treatment fascicle)" No. 06, Feb. 25, 1980 (Feb. 25, 1980), pp. 4-8.
Li, Wenzhen, Dyestuffs and Coloration, No. 04, Dec. 31, 1982 (Dec. 31, 1982), p. 61.

* cited by examiner

The concentration of acid lake blue A in a sodium alginate paste (gL$^{-1}$)

The concentration of acid lake blue A in a sodium alginate paste (gL$^{-1}$)

US 9,958,370 B2

METHOD FOR MEASURING DIFFUSION PERFORMANCE OF ACID DYE IN COLOR PASTE

This application is a national stage application of PCT/CN2014/084094, filed on Aug. 11, 2014, which claims priority to Chinese Patent Application No. 201410256338.3, filed on Jun. 10, 2014, which is incorporated by reference for all purposes as if fully set forth herein.

FIELD OF THE INVENTION

The present invention relates to the field of dye synthesis, and more particularly to a method for measuring the diffusion performance of an acid dye in a color paste.

DESCRIPTION OF THE RELATED ART

It is reported in domestic and foreign literatures that, research achievements on adsorption of a dye on a solid fiber surface and diffusion of a dye in the internal phase of fiber are well established in the modern basic dyeing theory of textiles. The adsorption of a dye on fiber macromolecules is generally divided into physical adsorption and chemical adsorption. The physical adsorption mainly involves van der Waals forces, hydrogen bonding or hydrophobic interactions between molecules, while the chemical adsorption is affected mainly by an ionic bond, a dative bond or a covalent bond, and the acting force is related to the nature of the chemical bonds (Adsorption and Diffusion in Dyeing and Printing Processes [M]. Beijing: The Textile Industry Press, 1985.144-149). Three typical adsorption isotherms of a dye on a fiber, i.e. Nernst adsorption, Langmuir adsorption and Freundlich adsorption, all are used to describe the relationship between the adsorption of a dye on a fiber and the concentration of a dye in an external medium (Dyeing and Finishing Process And Principles (Vol. 2) [M]. Beijing: The China Textile Press, 2009, 30-33). The diffusion of an adsorbed dye in a fiber internal phase is more complex and slower, and is a key stage determining the dyeing rate of the dye. For the diffusion of the adsorbed dye in the fiber, various adsorption forces between the dye and the fiber must be overcome, and the mechanical resistance caused by the chain network structure of fiber macromolecules and the possible repulsion force of partial function groups on the chain segments must also be overcome. In addition, loss of kinetic energy may also be arisen from the inelastic collision between the dye molecules and the fiber chain segments when the dye molecules diffuse and advance. Thus, the diffusion stage of the dye in the fiber internal phase is a critical stage of the dyeing rate.

The above theory also is applicable to the adsorption and diffusion stages of a dye on a fiber in the printing process. However, a medium where the dye is located during the printing process is a color paste made of a polymeric paste, which is significantly different from a solution medium in the dyeing process, and thus there is a substantial difference in transfer of the dye in the two media. As compared with the transfer of the dye in the solution medium, the transfer or diffusion of the dye in the color paste is much more complicated, affected by more factors, and the dye diffusion is more difficult. Hence, a substantial proportion of the dye remains in the color paste film, and this directly results in a low utilization of the dye in the printing process. Accordingly, the researches on the diffusion performance of the dye in the color paste are of important significance in the customization and control of the printing production process of textiles, and the improvement of the transfer utilization rate of the dye in the color paste.

However, at present, domestic and foreign theoretical studies on the diffusion performance of a dye in a printing color paste medium and a diffusion model thereof are comparatively rare. This may be because that during the actual operation of a printing process, the color paste film on a fabric surface is thin, and the transfer, adsorption and diffusion of the dye in the printing process mostly occur at a high temperature or high pressure in a single step, and thus there is a lack of a relevant effective experimental model or means.

SUMMARY OF THE INVENTION

An object of the present invention is to provide a method for measuring the diffusion performance of an acid dye in a color paste. the method of the invention has simple operation steps, reliable and safe experiments, highly stable test data and good reproducibility of results, and high temperature and high pressure are not required herein. Thus, the method is capable of accurately measuring the diffusion rate of a dye in a color paste, and has high sensitivity of the diffusion rate in the testing process, good selectivity for a particular dye, and capable of measuring the diffusion performance of all dyes other than disperse dyes in a color paste.

A method for measuring the diffusion performance of an acid dye in a color paste of the present invention includes the steps of:

A, preparing a primary paste with a solid content of 3-35% by slowly adding a suitable amount of a paste into a suitable amount of water under stirring, and placing the primary paste into a transparent cylindrical container and standing the primary paste to remove residual bubbles therein, so that an upper surface of the primary paste in the cylindrical container is flat, wherein the cylindrical container has an with an inner cross-sectional area S;

B, formulating a color paste by adding a dye to be measured into the primary paste obtained in the step A, and then flatly and uniformly paving a layer of the color paste with a volume of $V_0$ on the upper surface of the primary paste in the cylindrical container in the step A;

C, placing the cylindrical container with the paved color paste of the step B in an automatic temperature control device, and performing constant-temperature treatment at a temperature of 60-95° C., so that the dye in the color paste on the top of the blank primary paste in the cylindrical container diffuses downwards to the bottom of the cylinder, and determining the time t of downward diffusion of the dye in the color paste to the bottom of the cylinder;

D, sampling 0.1-1.0 g of the color paste with the dye being diffused from the bottom of the cylindrical container, and diluting the sampled color paste to 10-100 mL with deionized water, and determining the absorbance A of the dye in the solution at a characteristic wavelength by an ultraviolet-visible spectrophotometer;

E, formulating a series of color pastes with a concentration $C_i$ ($i=1, 2, 3 \ldots, n$) by respectively adding the dissolved dye to be measured into a suitable amount of the primary paste prepared in the step A, and measuring the absorbance $A_i$ ($i=1, 2, 3 \ldots, n$) corresponding to the series of dye concentrations using the same method as the step D, and obtaining a standard working curve equation $Y = c \times X + d$ for the concentration of the dye to be measured in the color paste and its absorbance by fitting; wherein Y is the absorbance value for the fitted working curve, X is the concentration of the dye in the color paste for the fitted working curve, and c and d are constants, obtainable by fitting the working curve;

F, determining the concentration b of the dye to be measured in the sampled color paste of the step D according to the standard working curve equation obtained in the step E; and G, calculating the number of moles of the diffused dye in the color paste diffused per unit area and per unit time, i.e. diffusion rate v, from the color paste volume $V_0$, the diffusion area S, the diffusion time t, and the concentration b of the dye in the sampled color paste obtained in the previous steps, by the formula:

$$v = \frac{b \times V_0}{M \times S \times t},$$

wherein, the diffusion rate v is expressed in mol/(m² s), the concentration b of the dye to be measured in the color paste is expressed in g $L^{-1}$, the volume $V_0$ of the applied color paste is expressed in L, the diffusion area S is the inner cross-sectional area of the transparent cylindrical container, expressed in m², the diffusion time t is expressed in sec (s), and M is the molar mass of the dye to be measured, expressed in g $mol^{-1}$.

Preferably, the paste in the step A is selected from the group consisting of sodium alginate, guar gum and carboxymethyl starch and any combination thereof.

Preferably, the primary paste in the step A contains an additive which is glycerol, urea or ammonium sulphate, wherein the molar concentration of glycerol is $7.0 \times 10^{-8}$ mol$L^{-1}$ to $5.0 \times 10^{-7}$ mol $L^{-1}$, the molar concentration of urea is $4.0 \times 10^{-7}$ mol $L^{-1}$ to $1.5 \times 10^{-6}$ mol $L^{-1}$, and the molar concentration of ammonium sulphate is $1.0 \times 10^{-7}$ mol $L^{-1}$ to $3.0 \times 10^{-7}$ mol $L^{-1}$.

More preferably, the molar concentration of glycerol is $9.0 \times 10^{-8}$ mol $L^{-1}$ to $3.0 \times 10^{-7}$ mol $L^{-1}$, the molar concentration of urea is $2.0 \times 10^{-7}$ mol $L^{-1}$ to $1.0 \times 10^{-6}$ mol $L^{-1}$, and the molar concentration of ammonium sulphate is $0.5 \times 10^{-7}$ mol $L^{-1}$ to $1.0 \times 10^{-7}$ mol$L^{-1}$, and the dye to be measured in the step B is an acid dye with a concentration of 4 g $L^{-1}$.

Preferably, the automatic temperature control device in the step C is a constant-temperature metal bath device. An insulation cover made of a transparent material is provided at the top of the constant-temperature metal bath device. At least one cylindrical container with an upper opening is provided in the constant-temperature metal bath device. The container is made of a transparent material, and a paste hole is opened at the bottom of the container, and a plug is provided at the paste hole.

Preferably, a temperature sensor probe is provided on a side wall of the container, and the container has a radius of 6.8 mm and a height of 50 mm.

More preferably, the paste hole is located at a center of the bottom of the container. More preferably, there are a plurality of temperature sensor probes spaced apart from each other from top to bottom.

Still more preferably, the number of the temperature sensor probes is 2-4.

The method for measuring the diffusion performance of an acid dye in a color paste of the present invention comprises the following steps: preparing a primary paste with a solid content of 3-35% from a paste, and then placing a part of the primary paste into a transparent cylindrical container and allowing to stand to remove residual bubbles in the primary paste, making an upper surface of the primary paste in the cylindrical container be flat; formulating a color paste by adding a dye to be measured into the primary paste, and then flatly and uniformly paving a layer of the color paste on the upper surface of the primary paste in the cylindrical container; placing the cylindrical container in an automatic temperature control device for constant-temperature treatment at a temperature of 60° C. to 95° C. for 1 to 5 h, so that the dye in the color paste on the top of the blank primary paste in the cylindrical container diffuses downwards to the bottom of the cylinder; and sampling 0.1 to 1.0 g of the primary paste from the bottom of the cylindrical container, and diluting the sampled primary paste to 10 to 100 mL with deionized water for determining the absorbance A of the dye in the solution at a characteristic wavelength by an ultraviolet-visible spectrophotometer; determining the concentration of the dye to be measured in the sampled color paste according to the standard working curve, and calculating the number of moles of the dye in the color paste diffused per unit area and per unit time, i.e. diffusion rate, from the known color paste concentration and color paste volume before diffusion, the diffusion area and the diffusion time.

By means of the above technical solutions, as compared with the prior art, the present invention has the following advantages: in technical principles, the present invention establishes for the first time an experimental model which facilitates the investigation and measurement of the diffusion performance of a dye in a color paste based on an actual printing process, meanwhile, the present invention suitably simplifies the factors affecting diffusion of the dye in the experimental model so that the technical solution is easily performed and developed, on the basis of main influencing factors in the actual printing process. In actual operation methods, the present invention has simple operation steps, reliable and safe experiments, highly stable test data and good reproducibility of results, and high temperature and high pressure are not required herein. The method has high sensitivity of the diffusion rate in the testing process, and good selectivity for a particular dye. As such, the present invention lays the groundwork for the development of theoretical studies of the diffusion performance and diffusion model of a dye in a printing color paste. Thus, the model of measuring the diffusion performance of a dye in a color paste of the present invention has simple operation steps, reliable and safe experiments, highly stable test data and good reproducibility of results, and high temperature and high pressure are not needed herein. The method is capable of accurately measuring the diffusion rate of a dye in a color paste, and has high sensitivity of the diffusion rate in the testing process, good selectivity for a particular dye, and capable of measuring the diffusion performance of all dyes other than disperse dyes in a color paste.

DESCRIPTION OF THE PREFERRED EMBODIMENTS

Figure 1:
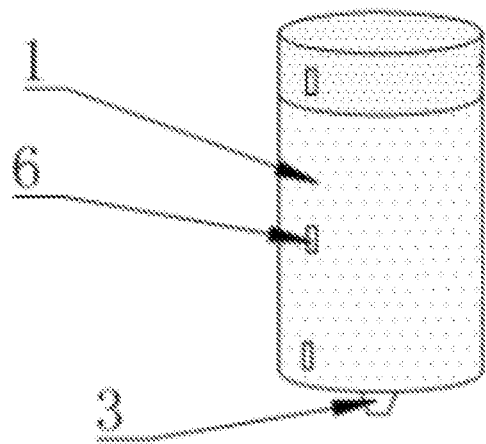
FIG. 1 is a schematic view of a container according to the present invention.

The invention will be further illustrated in more detail with reference to accompanying drawings. It is noted that, the following embodiments are intended for purposes of illustration only and are not intended to limit the scope of the invention.

The method for measuring the diffusion performance of an acid dye in a color paste of the present invention comprises the steps of:

A, preparing a primary paste with a solid content of 3-35% by slowly adding a suitable amount of a paste into a suitable amount of water under stirring, and placing the primary paste into a transparent cylindrical container and standing the primary paste to remove residual bubbles therein, so that an upper surface of the primary paste in the cylindrical container is flat, wherein the cylindrical container has an inner cross-sectional area S;

B, formulating a color paste by adding a dye to be measured into the primary paste obtained in the step A, and flatly and uniformly paving a layer of the color paste with a volume of $V_0$ on the upper surface of the primary paste in the cylindrical container of the step A;

C, placing the cylindrical container with the paved color paste of the step B in an automatic temperature control device, and performing for constant-temperature treatment at a temperature of 60° C.-95° C., so that the dye in the color paste on the top of the blank primary paste in the cylindrical container diffuses downwards to the bottom of the cylinder, and determining the time t of downward diffusion of the dye in the color paste to the bottom of the cylinder;

D, sampling 0.1-1.0 g of the color paste with the dye being diffused from the bottom of the cylindrical container, and diluting the sampled color paste to 10-100 mL with deionized water, and determining the absorbance A of the dye in the solution at a characteristic wavelength by an ultraviolet-visible spectrophotometer;

E, formulating a series of color pastes with a concentration Ci (i=1, 2, 3 . . . , n) by respectively adding the dissolved dye to be measured into a suitable amount of the primary paste prepared in the step A, and measuring the absorbance Ai (i=1, 2, 3 . . . , n) corresponding to the series of dye concentrations using the same method as the step D, and obtaining a standard working curve equation Y=c×X+d for the concentration of the dye to be measured in the color paste and its absorbance by fitting; wherein Y is the absorbance value for the fitted working curve, X is the concentration of the dye in the color paste for the fitted working curve, and c and d are constants, obtainable by fitting the working curve;

F, determining the concentration b of the dye to be measured in the sampled color paste of the step D according to the standard working curve equation obtained in the step E; and G, calculating the number of moles of the diffused dye in the color paste diffused per unit area and per unit time, i.e. diffusion rate v, from the color paste volume $V_0$, the diffusion area S, the diffusion time t, and the concentration b of the dye in the sampled color paste obtained in the previous steps, by the formula:

$$v = \frac{b \times V_0}{M \times S \times t}, \quad (1)$$

wherein, the diffusion rate v is expressed in mol/(m² s), the concentration b of the dye to be measured in the color paste is expressed in g $L^{-1}$, the volume $V_0$ of the applied color paste is expressed in L, the diffusion area S is the inner cross-sectional area of the transparent cylindrical container, expressed in m², the diffusion time t is expressed in sec (s), and M is the molar mass of the dye to be measured, expressed in g $mol^{-1}$.

In a preferable embodiment, the paste in the step A is selected from the group consisting of sodium alginate, guar gum and carboxymethyl starch and any combination thereof.

In a preferable embodiment, the primary paste in the step A contains an additive which is glycerol, urea or ammonium sulphate. The molar concentration of glycerol is $7.0 \times 10^{-8}$ mol $L^{-1}$ to $5.0 \times 10^{-7}$ mol $L^{-1}$, the molar concentration of urea is $4.0 \times 10^{-7}$ mol$L^{-1}$ to $1.5 \times 10^{-6}$ mol $L^{-1}$, and the molar concentration of ammonium sulphate is $1.0 \times 10^{-7}$ mol $L^{-1}$ to $3.0 \times 10^{-7}$ mol $L^{-1}$.

In a more preferable embodiment, the molar concentration of glycerol is $9.0 \times 10^{-8}$ mol $L^{-1}$ to $3.0 \times 10^{-7}$ mol $L^{-1}$, the molar concentration of urea is $2.0 \times 10^{-7}$ mol $L^{-1}$ to $1.0 \times 10^{-6}$ mol $L^{-1}$, and the molar concentration of ammonium sulphate is $0.5 \times 10^{-7}$ mol $L^{-1}$ to $1.0 \times 10^{-7}$ mol $L^{-1}$. The dye to be measured in the step B is an acid dye with a concentration of 4 g $L^{-1}$.

Figure 2:
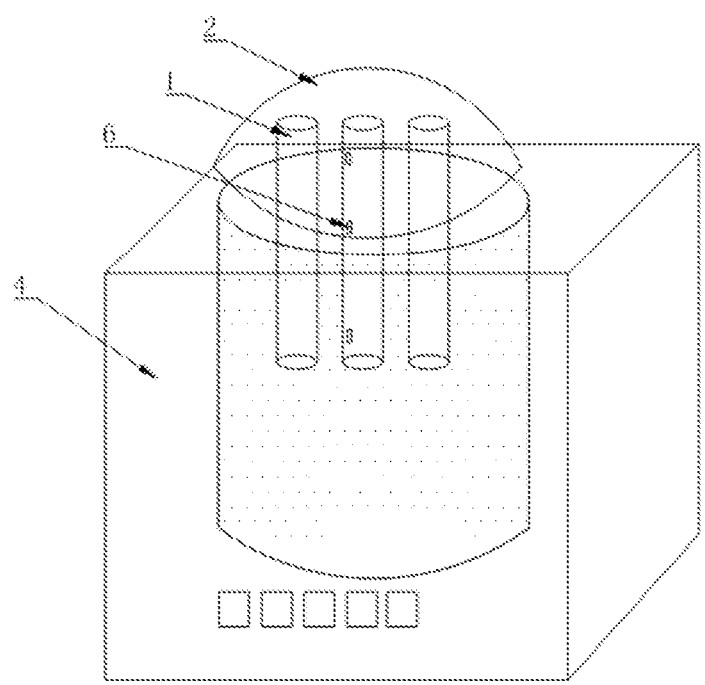
FIG. 2 is a schematic view of a model of measuring the diffusion performance of a dye in a color paste according to the present invention.

In a preferable embodiment, as shown in FIG. 1 and FIG. 2, the automatic temperature control device in the step C is a constant-temperature metal bath device 4. An insulation cover 2 is provided at the top of the constant-temperature metal bath device 4, and the insulation cover 2 is made of a transparent material. At least one cylindrical container 1 with an upper opening is provided in the constant-temperature metal bath device 4. The container 1 is made of a transparent material. A paste hole 3 is opened at the bottom of the container 1, and a plug is provided at the paste hole 3.

In a preferable embodiment, a temperature sensor probe 6 is provided on a side wall of the container 1, and the container 1 has a radius of 6.8 mm and a height of 50 mm.

In a more preferable embodiment, the paste hole 3 is located at a center of the bottom of the container 1.

In a still more embodiment, there are a plurality of temperature sensor probes 6 spaced apart from each other from top to bottom. The number of the temperature sensor probes 6 is 2-4.

Embodiment 1

6 g of a sodium alginate paste was weighted and slowly added into 94 mL of deionized water under stirring, to prepare a primary paste with a solid content of 6% for subsequent use. Then, 7.5 mL of the primary paste with a density of 1.73 g $mL^{-1}$ was taken out, and 0.03 g of dissolved acid lake blue A was added, after uniform stirring a color paste with a dye concentration of 4 g $L^{-1}$ was obtained for subsequent use.

Referring to FIG. 1, 1.73 g of the sodium alginate primary paste was placed into a transparent cylindrical container 1 with the specification of r=0.0068 m and 1=0.05 m, and then the primary paste was kept standing for 2 h to sufficiently remove residual bubbles therein, so that making an upper surface of the primary paste in the cylindrical container 1 is flat. 0.2 mL of the above color paste was flatly and uniformly applied on the upper surface of the primary paste in the cylindrical container 1, and then the cylindrical container 1 containing the color paste and the primary paste was placed into a constant-temperature metal bath device 4, as shown in FIG. 2, and the combination of the color paste and the primary paste was rapidly heated. The temperatures at three different positions in FIG. 1 were recorded by a thermograph, when the temperature at each position reached a target temperature of 80° C., the diffusion experiment of the dye began and timing was started. The diffusion of acid lake blue A in the container was recorded and observed, and when the acid lake blue A diffused to a lower surface of the primary paste in the cylindrical container 1, the needed time is t seconds. Then the container 1 was taken out, and a sampling hole 3 at the bottom of the container 1 was opened for sampling. After the certain amount of the sample was diluted, spectral analysis was performed by the UV-1810 ultraviolet-visible spectrophotometer, and the absorbance A of acid lake blue A at the maximum absorption wavelength was recorded.

Figure 3:
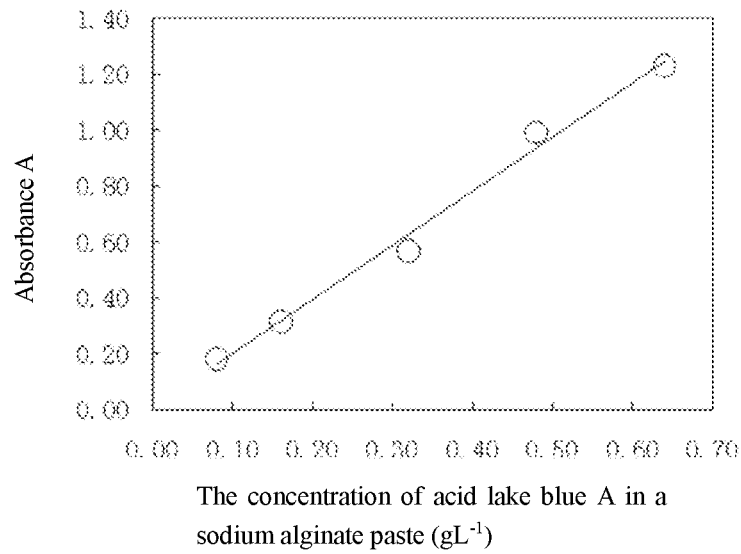
FIG. 3 is a concentration-absorbance standard curve of acid lake blue A in a sodium alginate paste.

Referring to FIG. 3, based on the absorbance measured for diluted sodium alginate color pastes with a series of known dye concentrations of $C_i$, a standard working curve of the absorbance and dye concentration was obtained, and the fitted equation was:

$$Y = 1.9350 \times X + 0.0075 \qquad (2)$$

wherein Y is the absorbance, and X is the concentration of acid lake blue A in the sodium alginate paste, expressed in $g\ L^{-1}$.

Then, according to the equation (2) and the measured absorbance A of the sampled color paste, the concentration of acid lake blue A to be measured in the actual sampled color paste could be calculated as b g $L^{-1}$. The diffusion rate v of acid lake blue A in the sodium alginate color paste was calculated according to the formula (1), from the known dye concentration (4.0 g $L^{-1}$) in the applied color paste, the volume $V_0$ ($2 \times 10^{-4}$ L) of the sampled color paste, the inner cross-sectional area S ($1.4375 \times 10^{-4}$ $m^2$) of the transparent cylindrical container 1, the molar mass M (690.80 g $mol^{-1}$) of acid lake blue A, and the diffusion time t ($1.248 \times 10^4$ s).

In terms of the steps and method described in the above embodiment, the diffusion rate of acid lake blue A in the sodium alginate paste at 80° C. was $3.302 \times 10^{-8}$ mol/($m^2$ s).

Embodiment 2

According to the method in the embodiment 1, the diffusion performance of acid lake blue A in a sodium alginate paste at 95° C. was measured. The diffusion time was $7.2 \times 10^3$ s and other experimental conditions and steps were the same as those in the embodiment 1.

Under the above conditions, the diffusion rate of acid lake blue A in the sodium alginate paste at 95° C. was measured as $5.57 \times 10^{-8}$ mol/($m^2$ s).

Embodiment 3

6 g of a sodium alginate paste was weighted and slowly added into 94 mL of deionized water under stirring, to prepare a blank paste with a solid content of 6%. Then, 99 g of the blank paste was taken out, and 1 g of glycerol was added, after uniform stirring, a primary paste with a glycerol concentration of $1.41 \times 10^{-7}$ mol $L^{-1}$ for subsequent use. Then, 7.5 mL of the primary paste with a density of 1.73 g $mL^{-1}$ was taken out, and 0.03 g of dissolved acid lake blue A was added, after uniform stirring a color paste with a dye concentration of 4 g $L^{-1}$ and the glycerol (additive) concentration of $1.41 \times 10^{-7}$ mol $L^{-1}$ for subsequent use.

According to the method in the embodiment 1, the diffusion performance of acid lake blue A in the sodium alginate paste with the glycerol concentration of $1.41 \times 10^{-7}$ mol $L^{-1}$ at 90° C. was measured. Other experimental conditions and steps were the same as those in the embodiment 1.

The diffusion rate of acid lake blue A in the sodium alginate paste at 90° C. was measured as $8.54 \times 10^{-8}$ mol/($m^2$ s), wherein the glycerol concentration in the sodium alginate paste is $1.41 \times 10^{-7}$ mol $L^{-1}$ and the diffusion time is $t = 7.8 \times 10^3$ s Embodiment 4

According to the method in the embodiment 3, the diffusion performance of acid lake blue A in a sodium alginate paste with a urea concentration of $6.49 \times 10^{-7}$ mol $L^{-1}$ at 90° C. was measured at the diffusion time of $7.2 \times 10^3$ s. Other experimental conditions and steps were the same as those in the embodiment 1.

Under the above conditions, the diffusion rate of acid lake blue A in the sodium alginate paste was measured as $1.244 \times 10^{-7}$ mol/($m^2$ s).

Embodiment 5

According to the method in the embodiment 3, the diffusion performance of acid lake blue A in a sodium alginate paste with an ammonium sulphate concentration of $1.48 \times 10^{-7}$ mol $L^{-1}$ at 90° C. was measured at the diffusion time of $5.8 \times 10^3$ s. Other experimental conditions and steps were the same as those in the embodiment 1.

Under the above conditions, the diffusion rate of acid lake blue A in the sodium alginate paste was measured as $1.061 \times 10^{-7}$ mol/($m^2$ s).

Embodiment 6

5 g of a sodium alginate paste was weighted and slowly added into 95 mL of deionized water under stirring, to prepare a primary paste with a solid content of 5% for subsequent use. Then, 7.5 mL of the primary paste with a density of 1.68 g $mL^{-1}$ was taken out, and 0.03 g of dissolved acid lake blue A was added, after uniform stirring a color paste with a dye concentration of 4.0 g $L^{-1}$ was obtained for subsequent use. According to the method in the embodiment 1, the diffusion performance of acid lake blue A in the sodium alginate primary paste was measured at 90° C. The diffusion time was $1.8 \times 10^3$ s and other experimental conditions and steps were the same as those in the embodiment 1.

Under the above conditions, the diffusion rate of acid lake blue A in the sodium alginate paste was measured as $2.13 \times 10^{-7}$ mol/($m^2$ s).

Embodiment 7

According to the method in the embodiment 3, the diffusion performance of acid lake blue A in a paste was measured at 90° C., wherein in the paste the concentration of the additive glycerol was $4.23 \times 10^{-7}$ mol $L^{-1}$ and the sodium alginate solid content is 6%. The diffusion time was $3.0 \times 10^3$ s, and other experimental conditions and steps were the same as those in the embodiment 1.

Under the above conditions, the diffusion rate of acid lake blue A in the sodium alginate paste was measured as $4.67 \times 10^{-7}$ mol/(m² s).

Embodiment 8

According to the method in the embodiment 3, the diffusion performance of acid lake blue A in a primary paste at 90° C. was measured, wherein in the primary paste the concentration of the additive ammonium sulphate is $2.95 \times 10^{-7}$ mol $L^{-1}$ and the sodium alginate solid content is 6%. The diffusion time was $2.1 \times 10^3$ s and other experimental conditions and steps were the same as those in the embodiment 1.

The diffusion rate of acid lake blue A in the sodium alginate primary paste at 90° C. was measured as $7.43 \times 10^{-7}$ mol/(m² s), wherein in the primary paste the concentration of ammonium sulphate is $2.951 \times 10^{-7}$ mol $L^{-1}$ and the solid content is 6%.

Embodiment 9

2.5 g of a guar gum paste was weighted and slowly added into 97.5 mL of deionized water under stirring, to prepare a primary paste with a solid content of 2.5% for subsequent use. Then, 7.5 mL of the primary paste with a density of 1.081 g mL$^{-1}$ was taken out, and 0.03 g of dissolved acid lake blue A was added, after uniform stirring a color paste with a dye concentration of 4 g L$^{-1}$ was obtained for subsequent use.

Referring to FIG. 1, 1.081 g of the guar gum primary paste was placed into a transparent cylindrical container 1 with the specification of r=0.0068 m and l=0.05 m, the experiment of diffusion rate of the dye to be measured was performed at 90° C., and other steps and process were the same as those in the embodiment 1.

Figure 4:
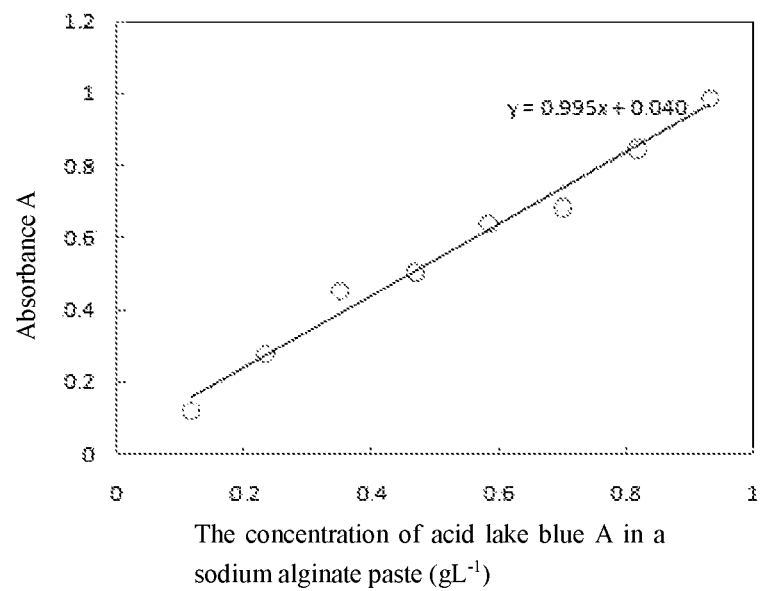
FIG. 4 is a concentration-absorbance standard curve of acid lake blue A in a guar gum paste.

Referring to FIG. 4, and the previous Detailed Description Of The Preferred Embodiments and the method in the embodiment 1, with based on the absorbances measured for diluted guar gum color pastes with a series of known dye concentrations of $C_i$, the fitted curve equation of the absorbance and dye concentration in the guar gum color paste was obtained:

$$Y = 0.995 \times X + 0.040 \qquad (3)$$

wherein Y is the absorbance, and X is the concentration of acid lake blue A in the guar gum paste, expressed in g L$^{-1}$.

Then, according to the equation (3) and the measured absorbance A of the sampled color paste, the concentration of acid lake blue A to be measured in the actual sampled color paste could be calculated as b g L$^{-1}$. With reference to the method in the embodiment 1, the diffusion rate v of acid lake blue A in the guar gum color paste was calculated according to the formula (1), from the known dye concentration (4.0 g L$^{-1}$) in the applied color paste, the volume $V_0$ ($2.0 \times 10^{-4}$ L) of the sampled color paste, the inner cross-sectional area S ($1.4375 \times 10^{-4}$ m²) of the transparent cylindrical container 1, the molar mass M (690.80 g mol$^{-1}$) of acid lake blue A, and the diffusion time t ($2.760 \times 10^3$ s).

In terms of the steps and method described in the above embodiment, the diffusion rate of acid lake blue A in the guar gum paste at 90° C. was $9.3874 \times 10^{-7}$ mol/(m² s).

Embodiment 10

According to the method in the embodiment 9, the diffusion performance of acid lake blue A in a guar gum paste was measured at 95° C. The diffusion time was $2.4 \times 10^3$ s and other experimental conditions and steps were the same as those in the embodiment 9.

Under the above conditions, the diffusion rate of acid lake blue A in the guar gum paste at 95° C. was measured as $1.1175 \times 10^{-6}$ mol/(m² s).

Embodiment 11

30 g of a carboxymethyl starch paste was weighted and slowly added into 70 mL of deionized water under stirring, to prepare a primary paste with a solid content of 30% for subsequent use. Then, 7.5 mL of the primary paste with a density of 1.222 g mL$^{-1}$ was taken out, and 0.03 g of dissolved acid lake blue A was added, after uniform stirring a color paste with a dye concentration of 4 g L$^{-1}$ was obtained for subsequent use.

Referring to FIG. 1, 1.222 g of the carboxymethyl starch primary paste was placed into a transparent cylindrical container 1 with the specification of r=0.0068 m and l=0.05 m, the experiment of diffusion rate of the dye to be measured was performed at 90° C., and other steps and process were the same as those in the embodiment 1.

With reference to the previous Detailed Description of the Preferred Embodiments and methods in the embodiment 1 and the embodiment 4, based on the absorbances measured for diluted carboxymethyl starch color pastes with a series of known dye concentrations of $C_i$, the fitted curve equation of the absorbance and the dye concentration in the carboxymethyl starch color paste was obtained:

$$Y = 1.069 \times X + 0.002 \qquad (4)$$

wherein Y is the absorbance, and X is the concentration of acid lake blue A in the carboxymethyl starch paste, expressed in g L$^{-1}$.

Then, according to the equation (4) and the measured absorbance A of the sampled color paste, the concentration of acid lake blue A to be measured in the actual sampled color paste could be calculated as b g L$^{-1}$. With reference to the method in the embodiment 1, the diffusion rate v of acid lake blue A in the carboxymethyl starch color paste was calculated according to the formula (1), from the known dye concentration (4.0 g L$^{-1}$) in the applied color paste, the volume $V_0$ ($2.0 \times 10^{-4}$ L) of the sampled color paste, the inner cross-sectional area S ($1.4375 \times 10^{-4}$ m²) of the transparent cylindrical container 1, the molar mass M (690.80 g mol$^{-1}$) of acid lake blue A, and the diffusion time t ($4.020 \times 10^3$ s).

According to the steps and methods described in the above embodiments, the diffusion rate of acid lake blue A in the carboxymethyl starch paste at 90° C. was $3.1013 \times 10^{-7}$ mol/(m² s).

The above preferred embodiments are described for illustration only, and are not intended to limit the scope of the invention. It should be understood, for a person skilled in the art, that various improvements or variations can be made herein without departing from the spirit and scope of the invention, and these improvements or variations should be covered within the protecting scope of the invention.

What is claimed is:

1. A method for measuring the diffusion performance of an acid dye in a color paste, comprising the steps of:
    A) preparing a primary paste with a solid content of 3-35% by adding a suitable amount of a paste into a suitable amount of water under stirring, and placing the primary paste into a transparent cylindrical container and standing the primary paste to remove residual bubbles therein, so that an upper surface of the primary paste in the cylindrical container is flat, wherein the cylindrical container has an inner cross-sectional area S;

B) formulating a color paste by adding a dye to be measured into the primary paste obtained in the step A, and flatly and uniformly paving a layer of the color paste with a volume of $V_0$ on the upper surface of the primary paste in the cylindrical container of the step A;

C) placing the cylindrical container with the paved color paste of the step B in an automatic temperature control device, and performing constant-temperature treatment at a temperature of 60° C.-95° C. so that the dye in the color paste on the top of the blank primary paste in the cylindrical container diffuses downwards to the bottom of the cylinder, and determining the time t of downward diffusion of the dye in the color paste to the bottom of the cylinder;

D) sampling 0.1-1.0 g of the color paste with the dye being diffused from the bottom of the cylindrical container, and diluting the sampled color paste to 10-100 mL with deionized water, and determining the absorbance A of the dye in the solution at a characteristic wavelength by an ultraviolet-visible spectrophotometer;

E) formulating a series of color pastes with a concentration $C_i$ (i=1, 2, 3 . . . , n) by respectively adding the dissolved dye to be measured into a suitable amount of the primary paste prepared in the step A, and measuring the absorbance $A_1$ (i=1, 2, 3 . . . , n) corresponding to the series of dye concentrations using the same method as the step D, and obtaining a standard working curve equation Y=c×X+d for the concentration of the dye to be measured in the color paste and its absorbance by fitting; wherein Y is the absorbance value for the fitted working curve, X is the concentration of the dye in the color paste for the fitted working curve, and c and d are constants, obtainable by fitting the working curve;

F) determining the concentration b of the dye to be measured in the sampled color paste of the step D according to the standard working curve equation obtained in the step E; and G) calculating the number of moles of the diffused dye in the color paste per unit area and per unit time, i.e. diffusion rate v, from the color paste volume $V_0$, the diffusion area S, the diffusion time t, and the concentration b of the dye in the sampled color paste obtained in the previous steps, by the formula:

$$v = \frac{b \times V_0}{M \times S \times t},$$

wherein, the diffusion rate v is expressed in mol/(m² s), the concentration b of the dye to be measured in the color paste is expressed in g $L^{-1}$, the volume $V_0$ of the applied color paste is expressed in L, the diffusion area S is the inner cross-sectional area of the transparent cylindrical container, expressed in m², the diffusion time t is expressed in sec (s), and M is the molar mass of the dye to be measured, expressed in g $mol^{-1}$.

2. The method for measuring the diffusion performance of an acid dye in a color paste as claimed in claim 1, wherein the paste in the step A is selected from the group consisting of sodium alginate, guar gum and carboxymethyl starch and any combination thereof.

3. The method for measuring the diffusion performance of an acid dye in a color paste as claimed in claim 1, wherein the primary paste in the step A contains an additive which is glycerol, urea or ammonium sulphate, the molar concentration of glycerol being $7.0 \times 10^{-8}$ mol$L^{-1}$ to $5.0 \times 10^{-7}$ mol $L^{-1}$, the molar concentration of urea being $4.0 \times 10^{-7}$ mol $L^{-1}$ to $1.5 \times 10^{-6}$ mol $L^{-1}$, and the molar concentration of ammonium sulphate being $1.0 \times 10^{-7}$ mol $L^{-1}$ to $3.0 \times 10^{-7}$ mol $L^{-1}$.

4. The method for measuring the diffusion performance of an acid dye in a color paste as claimed in claim 3, wherein the molar concentration of glycerol is $9.0 \times 10^{-8}$ mol $L^{-1}$ to $3.0 \times 10^{-7}$ mol $L^{-1}$, the molar concentration of urea is $2.0 \times 10^{-7}$ mol $L^{-1}$ to $1.0 \times 10^{-6}$ mol $L^{-1}$, and the molar concentration of ammonium sulphate is $0.5 \times 10^{-7}$ mol $L^{-1}$ to $1.0 \times 10^{-7}$ mol $L^{-1}$, and the dye to be measured in the step B being an acid dye with a concentration of 4 g $L^{-1}$.

5. The method for measuring the diffusion performance of an acid dye in a color paste as claimed in claim 1, wherein the automatic temperature control device in the step C is a constant-temperature metal bath device (4), an insulation cover (2) made of a transparent material being provided at the top of the constant-temperature metal bath device (4); at least one cylindrical container (1) with an upper opening is provided in the constant-temperature metal bath device (4), the container (1) being made of a transparent material, and a paste hole (3) is opened at the bottom of the container (1), and a plug being provided at the paste hole (3).

6. The method for measuring the diffusion performance of an acid dye in a color paste as claimed in claim 5, wherein a temperature sensor probe (6) is provided on a side wall of the container (1), and the container (1) has a radius of 6.8 mm and a height of 50 mm.

7. The method for measuring the diffusion performance of an acid dye in a color paste as claimed in claim 6, wherein the number of the temperature sensor probes (6) is 2-4.

8. The method for measuring the diffusion performance of an acid dye in a color paste as claimed in claim 5, wherein the paste hole (3) is located at a center of the bottom of the container (1).

9. The method for measuring the diffusion performance of an acid dye in a color paste as claimed in claim 5, wherein the container comprises a plurality of temperature sensor probes (6) spaced apart from each other from top to bottom.

* * * * *